United States Patent
Liu et al.

(10) Patent No.: US 9,551,680 B2
(45) Date of Patent: Jan. 24, 2017

(54) CHEMICALLY REACTIVE ENZYME IMMOBILIZATION

(71) Applicant: Verily Life Sciences LLC, Mountain View, CA (US)

(72) Inventors: Zenghe Liu, Mountain View, CA (US); Jeffrey George Linhardt, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 629 days.

(21) Appl. No.: 13/930,821

(22) Filed: Jun. 28, 2013

(65) Prior Publication Data

US 2015/0001072 A1 Jan. 1, 2015

(51) Int. Cl.
*G01N 27/327* (2006.01)
*C12Q 1/00* (2006.01)

(52) U.S. Cl.
CPC .............. *G01N 27/327* (2013.01); *C12Q 1/006* (2013.01)

(58) Field of Classification Search
CPC ..................................... G01N 27/327–27/3274
See application file for complete search history.

(56) References Cited

U.S. PATENT DOCUMENTS

| | | | |
|---|---|---|---|
| 5,683,563 A | 11/1997 | Mizutani | |
| 6,653,358 B2 | 11/2003 | Bruza | |
| 6,654,625 B1 | 11/2003 | Say | |
| 7,731,835 B2 | 6/2010 | Buck | |
| 8,385,998 B2 | 2/2013 | Zhang | |
| 8,437,829 B2 | 5/2013 | Mao | |
| 2009/0280181 A1 | 11/2009 | Slager | |
| 2010/0300897 A1 | 12/2010 | Savage | |
| 2011/0082356 A1 | 4/2011 | Yang et al. | |
| 2011/0136929 A1 | 6/2011 | Chow | |
| 2011/0152654 A1 | 6/2011 | Wang | |
| 2012/0116191 A1 | 5/2012 | Markle | |
| 2012/0186997 A1 | 7/2012 | Li et al. | |
| 2012/0245444 A1 | 9/2012 | Otis | |
| 2012/0283537 A1 | 11/2012 | Petisce | |
| 2012/0296186 A1 | 11/2012 | Ouyang | |
| 2013/0011460 A1 | 1/2013 | Liu | |

FOREIGN PATENT DOCUMENTS

WO    2012161735    11/2012

OTHER PUBLICATIONS

Akkaya, et al., "Functional polymer supports for immobilization of cholesterol oxidase", Biochemical Engineering Journal, vol. 43, No. 3, Mar. 2009, p. 333-337.*
International Search Report issued in connection with co-pending International Patent Application No. PCT/US2014/044608, ISA/KR dated Oct. 14, 2014, 6 pgs.
Written Opinion issued in connection with co-pending International Patent Application No. PCT/US2014/044608, ISA/KR dated Oct. 14, 2014, 5 pgs.
Gil, M.H., et al., "Immobilization of Glucose Oxidase on Thin-Film Gold Electrodes Produced by Magnetron Sputtering and Their Application in an Electrochemical Biosensor," Biotechnology Techniques, vol. 13, pp. 595-599 (1999).
Hall, C.E. et al., "Covalent Immobilisation of Glucose Oxidase on Methacrylate Copolymers for Use in an Amperometric Glucose Sensor," Analytica Chimica Acta, vol. 281, pp. 645-653 (1993).
Jusoh, Norhana et al., "Improvement of Glucose Biosensor Performances Using Poly(hydroxyethylmethacrylate) Outer Membrane," International Journal of Biology and Biomedical Engineering, Issue 1, vol. 6, pp. 77-86 (2012).
Slaughter, Gymama Ph.D., "Fabrication of Nanoindented Electrodes for Glucose Detection," Journal of Diabetes Science and Technology, vol. 4, Issue 2, pp. 320-327 (Mar. 2010).

* cited by examiner

*Primary Examiner* — J. Christopher Ball
(74) *Attorney, Agent, or Firm* — McDonnell Boehnen Hulbert & Berghoff

(57) ABSTRACT

An analyte sensor for the continuous or semi-continuous monitoring of physiological parameters and a method for making the analyte sensor are disclosed. The analyte sensor includes a crosslinked, hydrophilic copolymer sensing layer in contact with a surface of an electrode, where the sensing layer includes methacrylate-derived backbone chains having covalent bonds to an analyte sensing component. The method includes combining the precursor components of the sensing layer, depositing the combined mixture on a surface of an electrode, and curing the deposited mixture.

30 Claims, No Drawings

CHEMICALLY REACTIVE ENZYME IMMOBILIZATION

BACKGROUND

Unless otherwise indicated herein, the materials described in this section are not prior art to the claims in this application and are not admitted to be prior art by inclusion in this section.

The continuous or semi-continuous monitoring of physiological parameters has applications in many areas of modern medicine. Electrochemical-based sensors are believed to be particularly suitable for the monitoring and quantification of analytes (e.g., glucose) in bodily fluid samples (e.g., blood, tear film, urine or interstitial fluid samples). The use of an electrochemical-based sensor that employs an analyte sensing component, (e.g., an enzyme) in conjunction with an electrode(s) allows for the quantification of an analyte in a liquid sample by detecting the product(s) produced from the reaction of the analyte sensing component and the analyte.

SUMMARY

In one aspect, an analyte sensor is disclosed. The analyte sensor includes a crosslinked, hydrophilic copolymer sensing layer in contact with a surface of an electrode. The copolymer sensing layer includes backbone chains having first methacrylate-derived units and second methacrylate-derived units. Each first methacrylate-derived unit is covalently bound to an analyte sensing component, and the second methacrylate-derived units in different backbone chains are connected to one another by hydrophilic crosslinks, resulting in interconnected polymer chains. The sensor has third methacrylate-derived monomeric units, each having a hydrophilic side chain, present in the sensing layer or in a protective membrane provided on the sensing layer. The protective membrane is a crosslinked, hydrophilic copolymer having backbone chains of third methacrylate-derived monomeric units and fourth methacrylate-derived units, where the fourth methacrylate-derived units in different backbone chains are connected to one another by hydrophilic crosslinks.

In another aspect, a method for forming an analyte sensor is disclosed. The formation of the sensing layer can include forming a mixture including the precursor components of the sensing layer, depositing the mixture onto a surface of an electrode, and curing the deposited mixture. The mixture can include a methacrylate monomer covalently bound to an analyte sensing component, a dimethacrylate monomer, and an initiator. A methacrylate monomer having a hydrophilic side chain can be included in the mixture, or is included in a protective membrane provided on the sensing layer. The protective membrane can be formed by forming a mixture that includes a methacrylate monomer having a hydrophilic side chain, a dimethacrylate monomer and an initiator, depositing the mixture onto the sensing layer, and curing the deposited mixture.

These as well as other aspects, advantages, and alternatives, will become apparent to those of ordinary skill in the art by reading the following detailed description, with reference where appropriate to the accompanying drawings.

DETAILED DESCRIPTION

The method and system embodiments described herein are not meant to be limiting. It will be readily understood that certain aspects of the disclosed methods and systems can be arranged and combined in a wide variety of different configurations, all of which are contemplated herein.

In one aspect, an analyte sensor is disclosed. The analyte sensor includes:
a sensing layer in contact with a surface of an electrode, wherein the sensing layer includes:
  backbone chains including
    first methacrylate-derived monomeric units, each of which is covalently bound to an analyte sensing component through a hydrophilic linker, and
    second methacrylate-derived monomeric units,
  hydrophilic crosslinks between the second methacrylate-derived monomeric units in different backbone chains; and
  third methacrylate-derived monomeric units, each having a hydrophilic side chain,
where the third methacrylate-derived monomeric units are present in at least one of the sensing layer or an additional layer provided on the sensing layer.

In some embodiments, the analyte sensor can be an enzyme-based biosensor. These devices are able to convert an analyte-concentration-dependent biochemical reaction signal into a measurable physical signal, such as an optical or electrical signal. The biosensors can be used in the detection of analytes in clinical, environmental, agricultural and biotechnological applications. Analytes that can be measured in clinical assays of fluids of the human body include, for example, glucose, lactate, cholesterol, bilirubin, proteins, lipids and electrolytes. The detection of analytes in biological fluids, such as blood, tear film, or intestinal fluid, can be important in the diagnosis and the monitoring of many diseases.

In some embodiments, the analyte sensor can be a component of a body-mountable device, such as an eye-mountable, tooth-mountable, or skin-mountable device. The eye-mountable device can be configured to monitor health-related information based on one or more analytes detected in a tear film (the term "tear film" is used herein interchangeably with "tears" and "tear fluid") of a user wearing the eye-mountable device. For example, the eye-mountable device can be in the form of a contact lens that includes a sensor configured to detect one or more analytes (e.g., glucose). The eye-mountable device can also be configured to monitor various other types of health-related information.

In some embodiments, the body-mountable device may include a tooth-mountable device. The tooth-mountable device may take the form of or be similar in form to the eye-mountable device, and be configured to detect at least one analyte in a fluid (e.g., saliva) of a user wearing the tooth-mountable device.

In some embodiments, the body-mountable device may include a skin-mountable device. The skin-mountable device may take the form of or be similar in form to the eye-mountable device, and be configured to detect at least one analyte in a fluid (e.g., perspiration, blood, etc.) of a user wearing the skin-mountable device.

The sensor as described herein can include one or more conductive electrodes through which current can flow. Depending on the application, the electrodes can be configured for different purposes. For example, a sensor can include a working electrode, a reference electrode, and a counter-electrode. Also possible are two-electrode systems, in which the reference electrode serves as a counter-electrode. The working electrode can be connected to the reference electrode via a circuit, such as a potentiostat.

The electrode can be formed from any type of conductive material and can be patterned by any process that be used for patterning such materials, such as deposition or photolithography, for example. The conductive materials can be, for example, gold, platinum, palladium, titanium, carbon, copper, silver/silver-chloride, conductors formed from noble materials, metals, or any combinations of these materials. Other materials can also be envisioned.

The sensing layer of the analyte sensor can be a crosslinked, hydrophilic copolymer that includes backbone chains of first and second methacrylate-derived units and optionally third methacrylate-derived monomeric units. The first methacrylate-derived units of the backbone chains are each covalently bound to an analyte sensing component (e.g., an enzyme) through a hydrophilic linker. Each of the second methacrylate-derived units are covalently bound through a hydrophilic linker to another second methacrylate-derived unit in a different backbone chain. The crosslinks, or groups through which the second methacrylate-derived units of different backbone chains are connected to each other, are discussed in greater detail below. The optional third methacrylate-derived monomeric units each have a hydrophilic side chain. Various conformations and compositions of the linkers of the first methacrylate-derived units, and the crosslinks of the second methacrylate-derived units, and the side chains of the third methacrylate-derived units can be used to adjust the properties of the crosslinked, hydrophilic copolymer as desired, which include hydrophilicity, permeability and the ability to immobilize an analyte sensing component.

The sensor can also include a protective membrane provided on the sensing layer. For example, the protective membrane may be provided when the sensing layer lacks the third methacrylate-derived monomeric units. The protective membrane can be a crosslinked, hydrophilic copolymer having backbone chains of third and fourth methacrylate-derived monomeric units. Each of the third methacrylate-derived monomeric units have a hydrophilic side chain, and each of the fourth methacrylate-derived units are covalently bound through a hydrophilic linker to another fourth methacrylate-derived unit in a different backbone chain. The linkers, or groups through which the fourth methacrylate-derived units of different backbone chains are connected to each other, are herein referred to as "crosslinks".

In some embodiments, the first methacrylate-derived units can have the structure of formula (I):

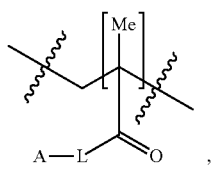

(I)

where L is a hydrophilic linker and A is an analyte sensing component. L can be water soluble or soluble in a water-miscible solvent, such as an alcohol. In some examples, L can have one or more heteroatoms, for example, nitrogen, oxygen or sulfur atoms. In some embodiments, L can have one or more hydroxy groups.

In some embodiments, L includes one or more alkylene oxide units. The alkylene oxide units can be derived from ethylene oxide, propylene oxide or butylene oxide, and can be a combination of two or three different alkylene oxide units. In some embodiments, the alkene oxide units form a poly(alkylene oxide) such as poly(ethylene glycol) or polypropylene glycol).

In certain embodiments, L can be $-L^1-L^2-$, where $L^2$ includes ethylene oxide units and $L^1$ is a linker derived from a reactive group. In such embodiments, the first methacrylate-derived units can have the structure of formula (Ia):

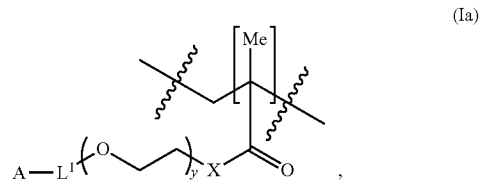

(Ia)

where X is —O—, —NR'— or —S—, and y is 0, 1, 2, 3, 4, 5, 6, 7, 8, 9 or 10.

$L^1$ can be a linker derived from any group that can undergo chemical reaction with one or more reactive groups of an analyte sensing component to form a covalent bond. The reactive groups can include carboxylate, hydroxyl, thiol and amino groups, such as the amine of a lysine amino acid in an enzyme.

In some embodiments, the $L^1$ is derived from a group having one or more epoxide groups. Chemical reaction of the epoxide with the reactive groups of an analyte sensing component can proceed through nucleophilic attack of the analyte sensor at the electrophilic epoxide carbon atom, providing a $L^1$ group having or more secondary alcohol moieties. In such embodiments, the first methacrylate-derived units can have the structure of formula (Ib):

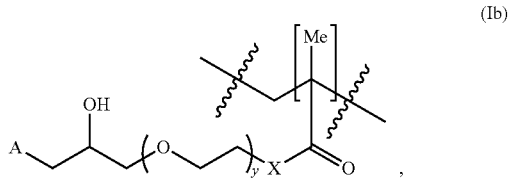

(Ib)

In some embodiments, the $L^1$ is derived from a group having one or more carboxylate groups. Chemical reaction of the carboxylate with the reactive groups of an analyte sensing component can provide an $L^1$ group having or more carboxylate moieties, such as an amide, ester or thioester. In such embodiments, the first methacrylate-derived units can have the structure of formula (Ic):

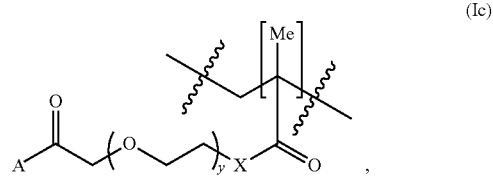

(Ic)

In some embodiments, the third methacrylate-derived units can have the structure of formula (II):

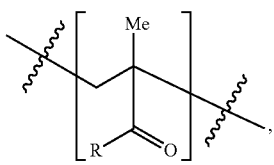
(II)

where R is a hydrophilic group. R can be water soluble or soluble in a water-miscible solvent, such as an alcohol. In some examples, R can have one or more heteroatoms, for example, nitrogen, oxygen or sulfur atoms. In some embodiments, L can have one or more hydroxy groups.

In some embodiments, R includes one or more alkylene oxide units. The alkylene oxide units can be derived from ethylene oxide, propylene oxide or butylene oxide, and can be a combination of two or three different alkylene oxide units. In some embodiments, the alkene oxide units form a poly(alkylene oxide) such as poly(ethylene glycol) or poly-propylene glycol).

In some embodiments, the third methacrylate-derived units can have the structure of formula (IIa):

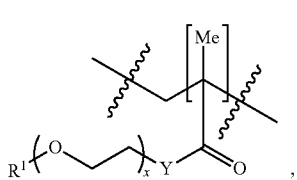
(IIa)

where Y is —O—, —NR'— or —S—, x is 0, 1, 2, 3, 4, 5, 6, 7, 8, 9 or 10 and $R^1$ is hydrogen, —$C_1$-$C_{12}$alkyl, —$C_1$-$C_{12}$alkyl-OH, —SiR'$_3$, —C(O)—$C_1$-$C_{12}$alkyl, —$C_1$-$C_{12}$alkyl-C(O)OR', where R' is hydrogen or —$C_1$-$C_{12}$alkyl.

In certain embodiments, the third methacrylate-derived units have the structure:

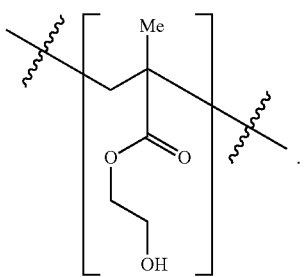

In some embodiments, the third methacrylate-derived units can have the structure of formula (IIb):

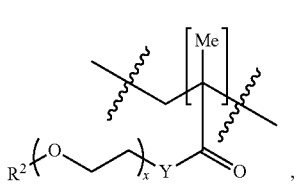
(IIb)

where Y is —O—, —NR'— or —S—, x is an average value of from about 2 to about 250, and $R^2$ is hydrogen, —$C_1$-$C_{12}$alkyl, —SiR'$_3$, —C(O)—$C_1$-$C_{12}$alkyl, —$C_1$-$C_{12}$alkyl-C(O)OR', where R' is hydrogen or —$C_1$-$C_{12}$alkyl.

In some embodiments, the third methacrylate-derived units can have the structure of formula (IIb), where Y and $R^2$ are as described above and x is such that the poly(ethylene glycol) has a number average molecular weight ($M_n$) of about 100 to about 10,000. In certain embodiments, x is selected so that the $M_n$ of the poly(ethylene glycol) falls within a range in Table 1.

TABLE 1

$M_n$ range of the poly(ethylene glycol) portion of the third methacrylate-derived units (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In certain embodiments, the analyte sensor has third methacrylate-derived units having the structure of formula (IIb), where Y is —O—, $R^2$ is methyl, and x is such that the poly(ethylene glycol) portion has a number average molecular weight ($M_n$) of about 500.

The crosslinks of the sensing layer and/or protective membrane are groups through which the second and/or fourth methacrylate-derived units of different backbone chains are connected to each other, and are represented by "A" in formula (III):

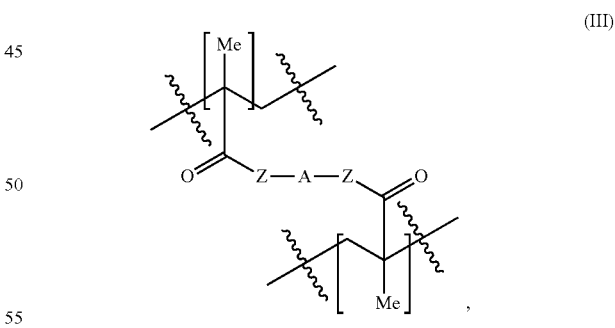
(III)

where Z is independently —O—, —NR'— or —S—, and A is a hydrophilic group.

In some embodiments, the crosslinks are hydrophilic. The crosslinks can be soluble in water or a water-miscible solvent, such as an alcohol. The crosslinks can have one or more heteroatoms, for example, nitrogen, oxygen or sulfur atoms. In some embodiments, the crosslinks have one or more hydroxy groups.

In some embodiments, the crosslinks include one or more alkylene oxide units. The alkylene oxide units can be in the form of a polymer, such as poly(ethylene glycol), poly (propylene glycol), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly (alkylene oxide) polymers. In certain embodiments, the poly(alkylene oxide) is a block copolymer of poly(ethylene glycol) and poly(propylene glycol). In other embodiments, the crosslinks include poly(ethylene glycol) (PEG).

In some embodiments, the crosslinks include one or more ethylene oxide units. For example, the crosslinks (e.g., A in formula (III) above) can have the structure of formula (IIIa):

(IIIa)

where w is 0, 1, 2, 3, 4, 5, 6, 7, 8, 9 or 10.

In certain embodiments, w is an average value of from about 2 to about 250.

In other embodiments, w in the crosslinks of formula (IIIa) is such that the number average molecular weight ($M_n$) of the PEG portion (within the brackets in formula (IIIa)) of the crosslinks is about 100 to about 10,000. For example, w can be selected such that the $M_n$ of the PEG portion of the crosslinks falls within a range in Table 2:

TABLE 2

$M_n$ range of the PEG portion of the crosslinks (values are approximate).

| Low | High |
| --- | --- |
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the crosslinks are derived from di(ethylene glycol) dimethacrylate, i.e., compounds of formula (III) or (IIIa) where Z is —O— and w is 1.

In some embodiments, the presence of the hydrophilic side chains of the third methacrylate-derived units in the sensing layer can form a porous network. The structure of the porous network includes regions within the copolymer that are not occupied by polymer. These regions are referred to herein as "pores" or "voids".

Similarly, when the sensor includes a protective membrane with third methacrylate-derived units, the hydrophilic side chains of the third methacrylate-derived units in the protective membrane can provide a protective membrane having a porous network.

The porous network of the protective membrane or the porous network formed in the sensing layer by the third methacrylate-derived units can facilitate control of the equilibrium between the concentration of the analyte (e.g., glucose) in the sample solution, and the analyte concentration in the proximity of the analyte sensor electrode surface. When all of the analyte arriving at the analyte sensor is consumed, the measured output signal can be linearly proportional to the flow of the analyte and thus to the concentration of the analyte. However, when the analyte consumption is limited by the kinetics of chemical or electrochemical activities in the analyte sensor, the measured output signal may no longer be controlled by the flow of analyte and may no longer be linearly proportional to the flow or concentration of the analyte. In this case, only a fraction of the analyte arriving at the analyte sensing component is consumed before the sensor becomes saturated, whereupon the measured signal stops increasing, or increases only slightly, with an increasing concentration of the analyte. The porous network can reduce the flow of the analyte to the analyte sensing component so the sensor does not become saturated and can therefore enable a wider range of analyte concentrations to be measured.

The hydrophilic properties of the side chain of the third methacrylate-derived units can be varied to produce desired properties of the porous network, such as permeability of the analyte. For example, flow of the analyte into or across the sensor can be dependent on the specific analyte being monitored, and thus, the porous network can be altered to obtain properties for monitoring a specific analyte. In some applications, the hydrophilicity of the porous network can be adjusted by changing the number alkylene oxide units in the side chain of the third methacrylate-derived units. Similarly, the hydrophilicity of the porous network can be adjusted by modifying the ratio of carbon atoms (i.e., —C—, —CH—, —CH$_2$— or —CH$_3$) to alkylene oxide units in the third methacrylate-derived units.

The analyte sensing component of the analyte sensor can be selected to monitor physiological levels of a specific analyte. For example, glucose, lactate, cholesterol and various proteins and lipids can be found in body fluids, including, for example, tear film, and can be indicative of medical conditions that can benefit from continuous or semi-continuous monitoring.

The analyte sensing component can be an enzyme selected to monitor one or more analytes. For example, physiological cholesterol levels can be monitored with cholesterol oxidase, lactate levels with lactate oxidase, and glucose levels with glucose oxidase or glucose dehydrogenase (GDH).

In some embodiments, the analyte sensing component can be an enzyme that undergoes a chemical reaction with an analyte to produce detectable reaction products. For example, a copolymer including glucose oxidase ("GOx") can be located on the working electrode to catalyze a reaction with glucose to produce hydrogen peroxide ($H_2O_2$). As shown below, the hydrogen peroxide can then be oxidized at the working electrode to releases electrons to the working electrode, which generates a current.

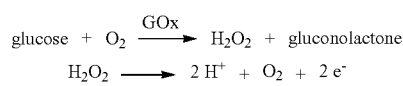

$$\text{glucose} + O_2 \xrightarrow{\text{GOx}} H_2O_2 + \text{gluconolactone}$$
$$H_2O_2 \longrightarrow 2H^+ + O_2 + 2e^-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

In other embodiments, the analyte sensing component is glucose dehydrogenase (GDH). In certain instances, the use of GDH can require the addition of a cofactor such as flavin adenine dinucleotide (FAD), nicotinamide adenine dinucleotide (NAD), flavin mononucleotide, pyrroloquinoline quinone (PQQ) or a coenzyme.

The thickness of the crosslinked, hydrophilic copolymer of the analyte sensor can vary depending on the desired properties of the analyte sensor, and whether a protective membrane is included. The thickness of the copolymer, as measured from the top of electrode to the top of the copolymer (or membrane), can play an important role in regulating the flow of the analyte to the analyte sensing component. Depending on the characteristics of the methacrylate-derived units in the copolymer, the type of analyte sensing component used, and the analyte to be monitored, the thickness of the copolymer can be from less than about 10 µm to about 30 µm. In some instances, the copolymer is less than 20 µm in thickness, where in other applications the copolymer is about 20 µm to about 25 µm in thickness. In certain applications, the copolymer is about 10 µm to about 15 µm in thickness, where in other applications the copolymer is about 15 µm to about 20 µm or about 25 µm to about 30 µm in thickness. In some embodiments, the copolymer is about 20 µm in thickness.

In another aspect, a method for making an analyte sensor is disclosed. The method can involve forming a crosslinked, hydrophilic copolymer sensing layer on a surface of an electrode, and optionally forming a crosslinked, hydrophilic copolymer protective membrane on the sensing layer. The method includes the formation of the sensing layer, including:

a) forming a first mixture including a first methacrylate monomer, a first dimethacrylate monomer, and a first initiator, where the first methacrylate monomer includes a covalent bond to an analyte sensing component;
 b) depositing the first mixture on a surface of an electrode;
 c) curing the first mixture to provide a sensing layer; and including a second methacrylate monomer in at least one of the first mixture or a second mixture deposited on the sensing layer.

In some embodiments of the method, the first mixture includes the second methacrylate monomer. In other embodiments, the second mixture includes the second methacrylate monomer.

In some embodiments of the method, the method further involves:

a) forming a second mixture including the second methacrylate monomer, a second dimethacrylate monomer, and a second initiator;
 b) depositing the second mixture onto the sensing layer; and
 c) curing the deposited second mixture to provide a protective membrane on the sensing layer.

The ratios of the combined components in the sensing layer and/or protective membrane can vary depending on the desired properties of the resulting analyte sensor. For example, adjusting the type and/or amount of first or second dimethacrylate monomer can alter the porous network of the resulting crosslinked, hydrophilic copolymer. Controlling the properties of the porous network can allow for the tuning of the permeability of the analyte sensor. Similar tunability can also be accomplished by adjusting the amount of the first and/or second mixtures deposited on the electrode and/or the sensing layer during the formation of the sensing layer and protective membrane, respectively.

The first and/or second mixture can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 3-[N-Tris(hydroxymethyl)methylamino]-2-hydroxypropanesulfonic acid (TAPSO), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), 2(R)-2-(methylamino)succinic acid, or phosphate buffered saline (PBS). In some embodiments, the mixtures are formed in a mixture of a buffered aqueous solution and ethanol.

In some embodiments of the method, the percentage of each component in the first and/or second mixture can be varied. In some instances, the percentage of the first monomer in the formation of the sensing layer is about 1% by weight to about 50% by weight, and the percentage of second methacrylate monomer is about 50% by weight to about 98% by weight. All percentages are given as a percentage of the cumulative amount of first monomer and second monomer in the mixture. For example, in certain examples, the percentage of the first methacrylate monomer is about 10%, and the amount of second methacrylate monomer is about 90%. The percentage of the first dimethacrylate monomer in the formation of the sensing layer, and/or percentage of the second dimethacrylate monomer in the formation of the protective membrane is about 0.1% by weight to about 15% by weight. The percentage of the first initiator in the formation of the sensing layer, and/or the percentage of the second initiator in the formation of the protective membrane is about 0.1% by weight to about 1% by weight. In certain embodiments, the first and/or second mixture is thoroughly mixed, optionally with a stirrer or shaker, before being deposited onto a surface of an electrode.

In some embodiments of the method, the first mixture can be formed by combining individual solutions having the components of the mixture. For example, the method can involve:

a) forming a first solution including the first methacrylate monomer, first dimethacrylate monomer, and first initiator;
 b) forming a second solution including the second methacrylate monomer, first dimethacrylate monomer, and first initiator;
 c) combining the first and second solutions to provide the first mixture of the method.

In some embodiments of the method, the first and second solutions of the method are formed with approximately the same concentration of first and second monomer, respectively. The percentage of each component can then be varied by adjusting the amounts each solution used to form the first mixture.

In some embodiments, the first mixture can be formed on a surface of an electrode. For example, each component, or a combination of one or more components, can be individually deposited to form the mixture. Similarly, when the mixture is formed by combining individual solutions, the solutions can be combined on a surface of an electrode to form the mixture.

In embodiments where the second mixture includes the second methacrylate monomer, the second mixture can be formed on the sensing layer. For example, each component, or a combination of one or more components, can be individually deposited onto the sensing layer to form the second mixture.

The first methacrylate monomer can be covalently bound to an analyte sensing component (e.g., an enzyme) through a hydrophilic linker. In some embodiments, the first methacrylate monomer can have the structure of formula (IV):

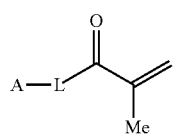

(IV)

where A is an analyte sensing component and L is selected to provide the first methacrylate-derived monomeric units described herein.

In certain embodiments, L can be -$L^1$-$L^2$-, where $L^2$ includes ethylene oxide units and $L^1$ is derived from a reactive group. In such embodiments, the first methacrylate monomer can have the structure of formula (IVa):

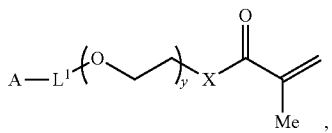

(IVa)

where X is —O—, —NR'— or —S—, and y is 0, 1, 2, 3 or 4.

$L^1$ can be a linker derived from any group that can undergo chemical reaction with one or more reactive groups of an analyte sensing component to form a covalent bond. The reactive groups can include carboxylate, hydroxyl, thiol and amino groups, such as an amine-containing amino acid of an enzyme.

In some embodiments, the $L^1$ is derived from a group having one or more epoxide groups. The monomer can be formed through an epoxide ring-opening reaction with the reactive groups of an analyte sensing component, providing a $L^1$ group having or more secondary alcohol moieties. In such embodiments, the first methacrylate monomer can have the structure of formula (IVb):

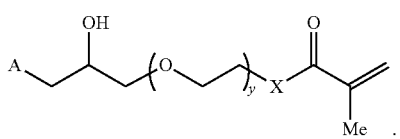

(IVb)

In some embodiments, the $L^1$ is derived from a group having one or more carboxylate groups. The monomer can be formed through reaction of the carboxylate with the reactive groups of an analyte sensing component can provide an $L^1$ group having one or more carboxylate moieties, such as an amide, ester or thioester. In such embodiments, the first methacrylate-derived units can have the structure of formula (IVc):

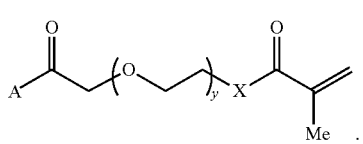

(IVc)

The second methacrylate monomer can have hydrophilic side chains that can have one or more heteroatoms. In certain embodiments, the side chains are selected to form the crosslinked, hydrophilic copolymer of the analyte sensor as described herein.

In some embodiments of the method, the second methacrylate monomer can have the structure of formula (V):

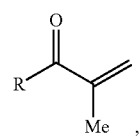

(V)

where R is a hydrophilic group. In certain embodiments of the method, the hydrophilic group includes one or more hydroxy groups, such as an alcohol.

In some embodiments of the method, the second methacrylate monomer has the structure of formula (Va):

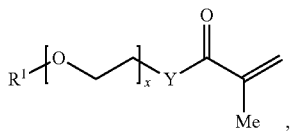

(Va)

where Y, x, $R^1$, and R' are selected to provide the third methacrylate-derived monomeric unit of the sensing layer or protective membrane, as described herein.

In certain embodiments of the method, the second methacrylate monomer has the structure:

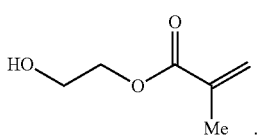

The first and/or second dimethacrylate monomer is a molecule having two terminal methacrylate groups tethered by a hydrophilic linker. The hydrophilic linker is selected to provide the crosslinks between the second or fourth methacrylate-derived units in different backbone chains of the sensing layer or protective membrane, respectively, as described herein.

The extent of crosslinking in the sensing layer or protective membrane of the analyte sensor can be controlled by adjusting the amount of first and/or second dimethacrylate monomer in the first or second mixture used to form the sensing layer and/or protective membrane, respectively. In some embodiments, the first and/or second dimethacrylate monomer is about 0.1% to about 15% of the mixture. In other examples, the amount is about 1% to about 5%, or about 5% to about 10%, or about 10% to about 15% of the mixture. In some embodiments, the amount is about 1%. In some instances, the first and second mixtures include about 1% of the first and second dimethacrylate monomer, respectively.

In some embodiments of the method, the first and/or second dimethacrylate monomer includes one or more alkylene oxide units to provide the crosslinks of the sensing layer and/or protective membrane as described herein. In some embodiments, the first and/or second dimethacrylate monomer includes poly(ethylene glycol) (PEG). For example, the dimethacrylate monomer can have the structure of formula (VI):

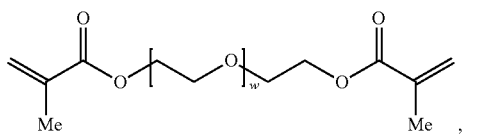

(VI)

where w is 0, 1, 2, 3, 4, 5, 6, 7, 8, 9 or 10.

In other embodiments of the method, the first and/or second dimethacrylate monomer can have the structure of formula (VI) where w is such that the number average molecular weight ($M_n$) of the PEG portion of the dimethacrylate monomer is about 100 to about 10,000. For example, w can be selected such that the $M_n$ of the PEG portion of dimethacrylate monomer falls within a range in Table 2. In some embodiments, the dimethacrylate monomer is di(ethylene glycol) dimethacrylate.

Depositing the mixture of sensing layer components onto a surface of an electrode, or the mixture of protective membrane components onto the cured sensing layer can be accomplished by a number of methods. For example, the depositing can be performed manually with a micro-syringe, or by automated fabrication processes with nano jet dispensing equipment.

In some embodiments of the method, the amount of the first mixture and/or the second mixture is selected to provide the desired thickness of the crosslinked, hydrophilic copolymer of the analyte sensor. In some embodiments, the amount deposited on the electrode and/or the cured sensing layer is about 50 nL/mm² to about 500 nL/mm². In other examples, the amount is about 50 μm to about 150 μm, or about 150 μm to about 300 μm, or about 300 μm to about 500 μm in thickness. In some embodiments, the amount is about 100 nL/mm². In some instances, depositing about 100 nL/mm² of a mixture including the first and second monomers provides a crosslinked, hydrophilic copolymer that is about 20 μm in thickness. In other embodiments, depositing about 20 nL/mm² of the first mixture, followed by depositing about 40 nL/mm² of a the second mixture provides a sensing layer and protective membrane with a combined thickness of about 20 μm.

Conditions suitable to initiate polymerization (i.e., curing) can be selected based on the characteristics of the initiator and the monomers being polymerized, but not to degrade the analyte sensing component. In embodiments where the analyte sensing component is an enzyme, the temperature and pH of the method can be selected to preserve the activity of the enzyme. In certain embodiments the initiator is activated with ultraviolet (UV) light. For example, when 2,2-diemthoxy-2-phenylacetophenone is used as an initiator, the curing can be performed with ultraviolet light.

EXAMPLES

Example 1

Covalent Linkage of GOx to a Methacrylate Monomer

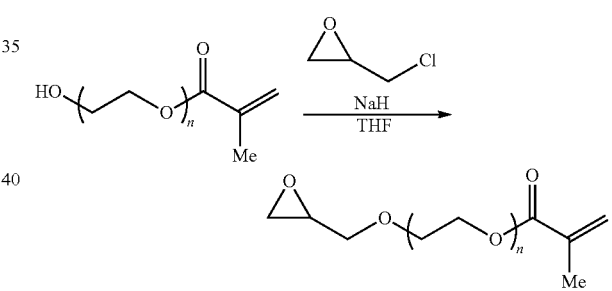

Methacrylate PEG-OH (Sigma Product #409529) is treated with NaH in THF and epichlorohydrin (Sigma Product #481386) is added to provide glycidyl-bound PEG methacrylate.

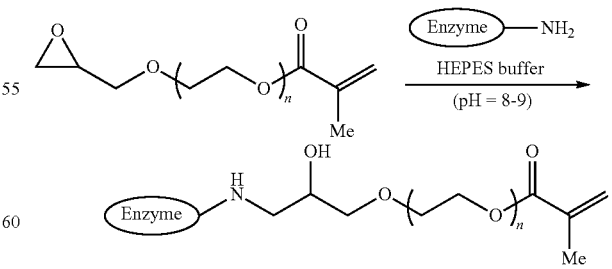

Glycidyl-bound PEG methacrylate is stirred in an HEPES buffer at a pH of 8-9 with an enzyme having at least one amino group, to provide an enzyme-bound PEG methacrylate monomer.

Example 2

Formation of a Single-Layer Analyte Sensor

Two (A and B) solutions are prepared:
A) enzyme-bound PEG methacrylate monomer from Example 1 in PBS buffer (pH=7.4) containing 1% by weight di(ethylene glycol) dimethacrylate and 1% by weight 2,2-dimethoxy-2-phenylacetophenone
B) poly(ethylene glycol) methyl ether methacrylate (average Mn 500, Aldrich product #447943) monomer solution containing 1% by weight di(ethylene glycol) dimethacrylate and 1% by weight 2,2-dimethoxy-2-phenylacetophenone.

A volume of each of the solutions (A-B) is combined and thoroughly mixed. A micro-syringe is used to deposit the solution onto a sensor electrode, and the deposited formulation is UV-cured for at 365 nm under nitrogen with an EC-500 light exposure chamber (Electro-Lite Corp).

Example 3

Formation of a Two-Layer Analyte Sensor

A solution of enzyme-bound PEG methacrylate monomer from Example 1 in PBS buffer (pH=7.4) containing 1% by weight di(ethylene glycol) dimethacrylate and 1% by weight 2,2-dimethoxy-2-phenylacetophenone (Solution A) is deposited onto a sensor electrode. The deposited solution is UV-cured for at 365 nm under nitrogen with an EC-500 light exposure chamber (Electro-Lite Corp).

A solution of poly(ethylene glycol) methyl ether methacrylate (average Mn 500, Aldrich product #447943) monomer containing 1% by weight di(ethylene glycol) dimethacrylate and 1% by weight 2,2-dimethoxy-2-phenylacetophenone (Solution B) is deposited onto cured Solution A. The deposited solution is UV-cured for at 365 nm under nitrogen with an EC-500 light exposure chamber (Electro-Lite Corp).

Example 4

Analyte Sensor Performance in a Glucose Solution

The analyte sensors formed in Example 2 and 3 are tested at various concentrations of analyte in phosphate buffered saline (PBS). The sensor is submerged in PBS and the analyte concentration is increased in a stepwise manner. The current generated at the electrode is measured using a potentiostat.

Although the crosslinked, hydrophilic copolymers in the above examples include methacrylate groups, there are a number of ethylenically unsaturated groups known in the art to be capable of undergoing polymerization. Ethylenically unsaturated monomers and macromers may be either acrylic- or vinyl-containing. Vinyl-containing monomers contain the vinyl grouping ($CH_2=CH-$), and are generally highly reactive. Acrylic-containing monomers are represented by the formula:

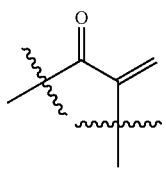 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked, hydrophilic copolymers by the polymerization of ethylenically unsaturated monomers and macromonomers, additional chemistries will be known to one or ordinary skill in the art to from such copolymers. As an example, epoxy chemistry, in which multifunctional amines and multifunctional epoxy compounds are mixed together and cured, can be used to form crosslinked, hydrophilic copolymers. Additionally, urethane chemistry may be used, in which multifunctional isocyanates are mixed with multifunctional alcohols and cured to provide crosslinked, hydrophilic copolymers. Other chemistries for the formation of crosslinked, hydrophilic copolymers exist, and will be well known to those of ordinary skill in the art.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

The invention claimed is:

1. An analyte sensor comprising:
a sensing layer in contact with a surface of an electrode, wherein the sensing layer comprises:
backbone chains comprising
first methacrylate-derived monomeric units, each of which is covalently bound to an analyte sensing component through a hydrophilic linker, and
second methacrylate-derived monomeric units;
hydrophilic crosslinks between the second methacrylate-derived units in different backbone chains; and
third methacrylate-derived monomeric units, each having a hydrophilic side chain,
wherein the third methacrylate-derived units are present in at least one of the sensing layer or an additional layer provided on the sensing layer; and
wherein the sensing layer has a thickness of about 10 μm to about 30 μm.

2. The sensor of claim 1, wherein the third methacrylate-derived monomeric units are present in the sensing layer.

3. The sensor of claim 1, wherein
the third methacrylate-derived monomeric units are present in an additional layer, and
the additional layer is a protective membrane comprising:
backbone chains comprising;
third methacrylate-derived monomeric units, each unit having a hydrophilic side chain, and
fourth methacrylate-derived monomeric units; and
hydrophilic crosslinks between the fourth methacrylate-derived units in different backbone chains.

4. The sensor of claim 1, wherein the first methacrylate-derived monomeric units have the structure of formula (I):

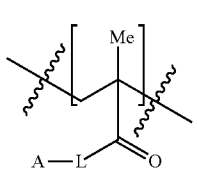

(I)

wherein L is a hydrophilic linker and A is an analyte sensing component.

5. The sensor of claim 1, wherein the first methacrylate-derived units have the structure of formula (Ia):

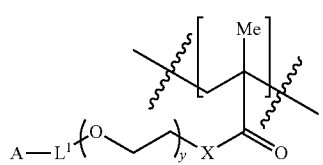

(Ia)

wherein
X is —O—, —NR'— or —S—,
wherein R' is hydrogen or —C$_1$-C$_{12}$alkyl;
y is 0-10;
L$^1$ is a linker; and
A is an analyte sensing component.

6. The sensor of claim 1, wherein the third methacrylate-derived units have the structure of formula (IIa):

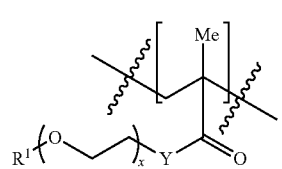

(IIa)

wherein
Y is —O—, —NR'— or —S—;
x is 0-10; and
R$^1$ is hydrogen, —C$_1$-C$_{12}$alkyl, —C$_1$-C$_{12}$alkyl-OH, —SiR'$_3$, —C(O)—C$_1$-C$_{12}$alkyl, —C$_1$-C$_{12}$alkyl-C(O)OR';
wherein each R' is independently hydrogen or —C$_1$-C$_{12}$alkyl.

7. The sensor of claim 1, wherein the third methacrylate-derived units have the structure:

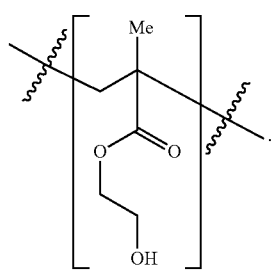

.

8. The sensor of claim 1, wherein the third methacrylate-derived units have the structure of formula (IIb):

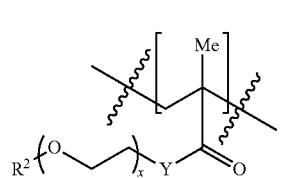

(IIb)

wherein
Y is —O—, —NR'— or —S—;
x is an average value of from about 2 to about 250; and
R$^2$ is hydrogen, —C$_1$-C$_{12}$alkyl, —C$_1$-C$_{12}$alkyl-OH, —SiR'$_3$, —C(O)—C$_1$-C$_{12}$alkyl, —C$_1$-C$_{12}$alkyl-C(O)OR';
wherein each R' is independently hydrogen or —C$_1$-C$_{12}$alkyl.

9. The sensor of claim 1, wherein the hydrophilic crosslinks between the second or fourth methacrylate-derived units in different backbone chains comprise one or more alkylene oxide units.

10. The sensor of claim 1, wherein the hydrophilic crosslinks between the second or fourth methacrylate-derived units in different backbone chains have the structure of formula (IIIa):

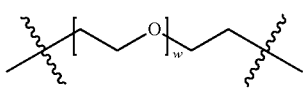

(IIIa)

wherein w is 1-10.

11. The sensor of claim 1, wherein the hydrophilic crosslinks between the second or fourth methacrylate-derived units in different backbone chains have the structure of formula (IIIa):

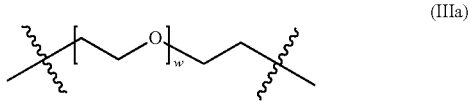

(IIIa)

wherein w is an average value of from about 2 to about 250.

12. The sensor of claim 1, wherein the hydrophilic crosslinks between the second or fourth methacrylate-derived units in different backbone chains are derived from the di(ethylene glycol) portion of di(ethylene glycol) dimethacrylate.

13. The sensor of claim 1, wherein the analyte sensing component comprises glucose oxidase.

14. The sensor of claim 2, wherein the sensing layer comprises:

first methacrylate-derived monomeric units having the structure of formula (I):

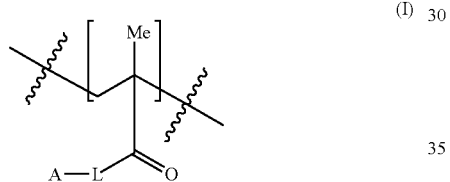

(I)

wherein L is a hydrophilic linker and A is an analyte sensing component;

third methacrylate-derived monomeric units having the structure of formula (IIb):

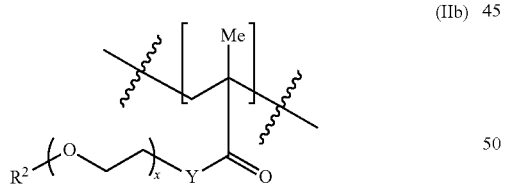

(IIb)

wherein
Y is —O—, —NR'— or —S—;
x is an average value of from about 2 to about 250; and
$R^2$ is hydrogen, —$C_1$-$C_{12}$alkyl, —$C_1$-$C_{12}$alkyl-OH, —$SiR'_3$, —C(O)—$C_1$-$C_{12}$alkyl, —$C_1$-$C_{12}$alkyl-C(O)OR';
wherein each R' is independently hydrogen or —$C_1$-$C_{12}$alkyl; and
crosslinks between the second methacrylate-derived units in different backbone chains having the structure of formula (IIIa):

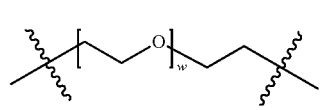

(IIIa)

wherein w is an average value of from about 2 to about 250.

15. The analyte sensor of claim 3, wherein
the sensing layer comprises:
first methacrylate-derived monomeric units having the structure of formula (I):

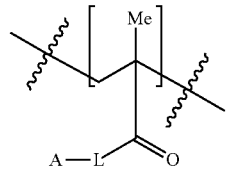

(I)

wherein L is a hydrophilic linker and A is an analyte sensing component; and
crosslinks between the second methacrylate-derived units in different backbone chains having the structure of formula (IIIa):

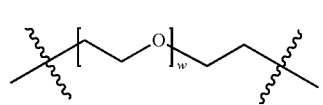

(IIIa)

wherein w is an average value of from about 2 to about 250; and
the protective membrane comprises:
third methacrylate-derived monomeric units having the structure of formula (IIb):

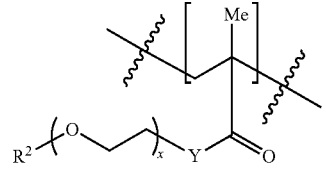

(IIb)

wherein
Y is —O—, —NR'— or —S—;
x is an average value of from about 2 to about 250; and
$R^2$ is hydrogen, —$C_1$-$C_{12}$alkyl, —$C_1$-$C_{12}$alkyl-OH, —$SiR'_3$, —C(O)—$C_1$-$C_{12}$alkyl, —$C_1$-$C_{12}$alkyl-C(O)OR';
wherein each R' is independently hydrogen or —$C_1$-$C_{12}$alkyl; and
crosslinks between the fourth methacrylate-derived units in different backbone chains having the structure of formula (IIIa):

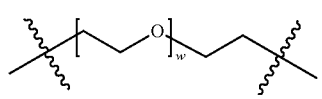

wherein w is an average value of from about 2 to about 250.

16. A method of making an analyte sensor, comprising:
forming a first mixture comprising a first methacrylate monomer, a first dimethacrylate monomer, and a first initiator, wherein the first methacrylate monomer has a covalent bond to an analyte sensing component;
depositing the first mixture on a surface of an electrode;
curing the deposited first mixture to provide a sensing layer; and
including a second methacrylate monomer in at least one of the first mixture or a second mixture deposited on the sensing layer,
wherein the sensing layer has a thickness of about 10 μm to about 30 μm.

17. The method of claim 16, wherein the first mixture further comprises the second methacrylate monomer.

18. The method of claim 16, further comprising:
forming a second mixture comprising the second methacrylate monomer, a second dimethacrylate monomer, and a second initiator;
depositing the second mixture onto the sensing layer; and
curing the deposited second mixture to provide a protective membrane on the sensing layer.

19. The method of claim 16, wherein the first methacrylate monomer has the structure of formula (IV):

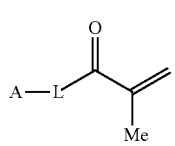

wherein L is a hydrophilic linker and A is an analyte sensing component.

20. The method of claim 16, wherein the first methacrylate monomer have the structure of formula (IVa):

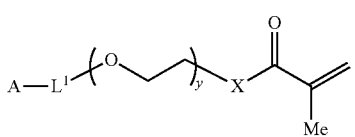

wherein
X is —O—, —NR'— or —S—,
wherein R' is hydrogen or —$C_1$-$C_{12}$alkyl;
y is 0-10;
$L^1$ is a linker; and
A is an analyte sensing component.

21. The method of claim 16 or 18, wherein the second methacrylate monomer has the structure of formula (Va):

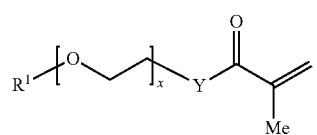

wherein
Y is —O—, —NR'— or —S—;
x is 0-10; and
$R^1$ is hydrogen, —$C_1$-$C_{12}$alkyl, —$C_1$-$C_{12}$alkyl-OH, —$SiR'_3$, —C(O)—$C_1$-$C_{12}$alkyl, —$C_1$-$C_{12}$alkyl-C(O)OR';
wherein each R' is independently hydrogen or —$C_1$-$C_{12}$alkyl.

22. The method of claim 16 or 18, wherein the second methacrylate monomer has the structure:

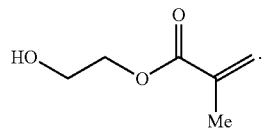

23. The method of claim 16 or 18, wherein the second methacrylate monomer has the structure of formula (Va):

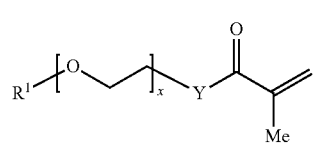

wherein
Y is —O—, —NR'— or —S—;
x is an average value of from about 2 to about 250; and
$R^1$ is hydrogen, —$C_1$-$C_{12}$alkyl, —$C_1$-$C_{12}$alkyl-OH, —$SiR'_3$, —C(O)—$C_1$-$C_{12}$alkyl, —$C_1$-$C_{12}$alkyl-C(O)OR';
wherein each R' is independently hydrogen or —$C_1$-$C_{12}$alkyl.

24. The method of claim 16 or 18, wherein the first or second dimethacrylate monomer comprises alkylene oxide units.

25. The method of claim 16 or 18, wherein the first or second dimethacrylate monomer has a structure of formula (VI):

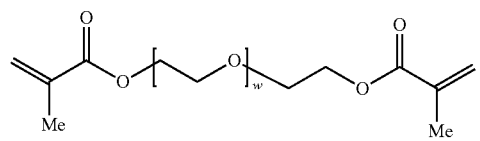

wherein w is 1-10.

26. The method of claim 16 or 18, wherein the first or second dimethacrylate monomer has a structure of formula (VI):

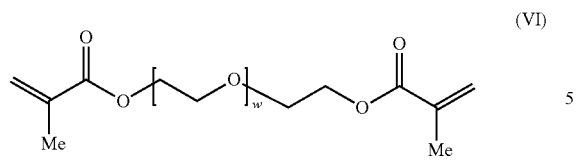

(VI)

wherein w is an average value of from about 2 to about 250.

27. The method of claim 16 or 18, wherein the first or second dimethacrylate monomer is di(ethylene glycol) dimethacrylate.

28. The method of claim 16, wherein the analyte sensing component comprises glucose oxidase.

29. The method of claim 16 or 18, wherein curing the deposited first or second mixture comprises exposing the deposited first or second mixture to ultraviolet light.

30. The method of claim 16 or 18, wherein first or second initiator is 2,2-dimethoxy-2-phenylacetophenone.

\* \* \* \* \*